(12) United States Patent
Frueh et al.

(10) Patent No.: US 10,545,121 B2
(45) Date of Patent: Jan. 28, 2020

(54) PIPELINE INSPECTION SYSTEMS AND METHODS

(71) Applicant: PII Pipetronix GmbH, Stutensee (DE)

(72) Inventors: Volker Frueh, Stutensee (DE); Heiko Witte, Stutensee (DE)

(73) Assignee: PII Pipetronix GmbH, Stutensee (DE)

( * ) Notice: Subject to any disclaimer, the term of this patent is extended or adjusted under 35 U.S.C. 154(b) by 0 days.

(21) Appl. No.: 15/987,578

(22) Filed: May 23, 2018

(65) Prior Publication Data
US 2019/0360976 A1    Nov. 28, 2019

(51) Int. Cl.
*G01N 29/265* (2006.01)
*G01N 29/24* (2006.01)

(52) U.S. Cl.
CPC ....... *G01N 29/265* (2013.01); *G01N 29/2406* (2013.01); *G01N 2291/2636* (2013.01)

(58) Field of Classification Search
CPC ............. G01N 29/265; G01N 29/2406; G01N 29/2412; G01N 29/2462; G01N 29/043; G01N 2291/2636; G01N 2291/106
USPC .................................. 73/592, 622, 623, 644
See application file for complete search history.

(56) References Cited

U.S. PATENT DOCUMENTS

| | | |
|---|---|---|
| 4,807,484 A | 2/1989 | Goedecke |
| 2005/0126316 A1 | 6/2005 | Richter et al. |
| 2008/0042646 A1* | 2/2008 | Burkhardt .............. G01N 27/82 324/240 |
| 2009/0158850 A1* | 6/2009 | Alleyne ............... G01N 29/221 73/623 |
| 2012/0325004 A1 | 12/2012 | Herron et al. |
| 2013/0025370 A1 | 1/2013 | Herron et al. |
| 2013/0133429 A1 | 5/2013 | Palma et al. |
| 2014/0015521 A1* | 1/2014 | Laursen ................. G01N 27/82 324/220 |
| 2016/0273992 A1 | 9/2016 | Frueh |

OTHER PUBLICATIONS

Extended European Search Report and Opinion issued in connection with corresponding EP Application No. 18174117.4 dated Jan. 4, 2019.

* cited by examiner

*Primary Examiner* — Suman K Nath
(74) *Attorney, Agent, or Firm* — Mintz Levin Cohn Ferris Glovsky and Popeo, P.C.

(57) ABSTRACT

Pipeline inspection systems are provided. In one embodiment, a pipeline inspection system can include at least one sensor module having a module body and a plurality of sensor holders mounted to the module body. Each sensor holder can include a holder body with a first body end, a second body end, and a plurality of sensors positioned therebetween, and a plurality of rotational guides that can be coupled to the holder body and configured to be biased towards an interior surface of the pipeline wall so as to define a standoff distance between each sensor and the interior surface of the pipeline wall. Each sensor holder can be at least partially pivotable about a longitudinal axis of the holder body extending between the first body end and the second body end. Methods of inspecting a pipeline are also provided.

18 Claims, 11 Drawing Sheets

PIPELINE INSPECTION SYSTEMS AND METHODS

BACKGROUND

Inspection of a pipeline can sometimes be performed using a system, commonly referred to as a pipeline inspection gauge or "PIG," which travels inside the pipeline. As an example, a PIG can include one or more sensor modules having sensors arranged for measuring or detecting wall thickness or defects in the wall of the pipeline.

In some instances, the sensors (e.g., ultrasonic sensors, magnetic sensors, etc.) can be mounted on sensor holders of the sensor module(s). The sensor holders can be configured to position the sensors adjacent to the pipe wall at a set inclination angle when, for example, the sensor module(s) carries out an inspection run through a pipeline. These sensor holders can include skids formed of flexible material (e.g., an elastomer). The skids can often be arranged left and right of the sensors, front and back of the sensors, or both. A skid can be configured to run immediately adjacent to or in contact with an inner surface of the pipe, with the sensors arranged at a standoff distance from the outer surface of the skid, in order to protect the sensors against wear or other damage from contact with the pipe and set a given standoff distance. Further, the flexibility of the skid can allow a sensor holder to travel through bends and other pipeline features.

SUMMARY

Pipeline inspection systems are provided. In some instances, the pipeline inspection modules including a sensor module do not provide clear or accurate data. For instance, when passing the sensor module(s) through the pipeline, frictional drag between the skids and the interior surface of the pipeline can cause the sensor holders (and the sensors) to pull away from the wall of the pipeline, moving the sensors out of a desired sensing position, thereby reducing the quality of acquired sensory data. Moreover, over time, wear and deterioration of the skids can be observed. Even minimal abrasion of the skids can adversely affect the accuracy of the sensor measurements, and can prevent the sensor modules from successfully passing through portions the pipeline (e.g., sections of the pipeline in which the inside diameter of the pipeline changes). For example, an uneven abrasion of the skids can reduce the standoff distance from the sensors to the pipe wall, and consequently, the desired set inclination angle of the sensors. Alternatively, or additionally, the flexibility of the skid material can result in uncontrolled deformations of the shape of the skid, which in turn can cause skid liftoff from the interior surface of the pipe wall and deviations in the set inclination angle of the sensors.

In one exemplary embodiment, a pipeline inspection system can include at least one sensor module having a module body extending from a first module end to a second module end, and a plurality of sensor holders mounted to the module body. Each sensor holder can include a holder body with a first body end, a second body end, and a plurality of sensors positioned therebetween, and a plurality of rotational guides in which each sensor holder can be at least partially pivotable about a longitudinal axis of the holder body extending between the first body end and the second body end. The plurality of sensors can be configured to sense a parameter of a wall of a pipeline having a longitudinal axis extending therethrough. The plurality of rotational guides can be coupled to the holder body and configured to be biased towards an interior surface of the pipeline wall so as to define a standoff distance between each sensor and the interior surface of the pipeline wall.

In another embodiment, the pipeline inspection system can include a drawbar coupled to an axle extending through the first and second rotational guides and coupled to the first body end to allow the holder body to at least partially pivot about the longitudinal axis of the holder body.

In some embodiments, the plurality of rotational guides can include a first rotational guide and a second rotational guide coupled to the first body end, and a third rotational guide and a fourth rotational guide coupled to the second body end. In one embodiment, the first and third rotational guides can be longitudinally aligned relative to each other such that the third rotational guide follows substantially the same path as the first rotational guide when the at least one sensor module translates through the pipeline. In another embodiment, the second and fourth rotational guides can be longitudinally aligned relative to each other such that the fourth rotational guide follows substantially the same path as the second rotational guide when the at least one sensor module translates through the pipeline.

In another embodiment, the plurality of sensors can be positioned in a predetermined pattern such that when at least one of the plurality of rotational guides contacts a feature on the interior surface of a pipeline, a first sensor of the plurality of sensors tilts relative to the longitudinal axis of the pipeline from an initial position to a deviated position while at least one of the other plurality of sensors is in the initial position when sensing the parameter of the pipeline wall.

In another embodiment, each sensor holder can include at least one suspension arm mounted between the module body and the sensor holder that is configured to bias at least one of the plurality of rotational guides into contact with the pipeline wall.

In another embodiment, the at least one sensor holder of the plurality of sensor holders can include at least one protection member that can be configured to prevent damage to the plurality of sensors as the at least one sensor module translates though the pipeline.

In another embodiment, the at least one sensor module can have a module longitudinal axis extending between the first and second module ends, and the at least one sensor module can include a supporting member that is configured to substantially align and overlap the module longitudinal axis with the longitudinal axis of the pipeline when the at least one sensor module is translated through the pipeline.

In another embodiment, the at least one sensor module can have a module longitudinal axis extending between the first and second module ends, and the plurality of sensor holders can be spaced circumferentially from one another about the longitudinal axis of the at least one sensor module.

In another embodiment, the at least one sensor module can include first and second sensor modules that can be axially offset from one another with respect to the longitudinal axis of the pipeline wall.

In another embodiment, the at least one sensor module can include first and second sensor modules, and the plurality of sensor holders of the first sensor module can be out of phase with the plurality of sensors holders of the second sensor module such that the system has about 360 degrees of inspection coverage of the pipeline wall when the first and second sensor modules translate through the pipeline.

In another embodiment, the at least one sensor module can include first and second sensor modules in which the plurality of sensors of the first sensor module can be angled in a first direction and the plurality of sensors of the second sensor module can be angled in a second direction opposite the first direction.

Methods for inspecting a pipeline is also provided. In one exemplary embodiment, the method can include advancing at least one sensor module in a downstream direction through a pipeline having a longitudinal axis extending therethrough. The at least one sensor module can have a plurality of sensor holders in which each sensor holder can include a holder body with a plurality of sensors. Each holder body can include a plurality of rotational guides that are biased toward a wall of the pipeline so as to define a standoff distance between each sensor and an interior surface of the pipeline wall. Each holder body can be pivoting about a longitudinal axis thereof such that at least one of the plurality of rotational guides remains in contact with the interior surface of the pipeline wall as the at least one sensor module translates through the pipeline. The method can also include sensing, by the plurality of sensors, a parameter of the pipeline wall as the at least one sensor module translates through the pipeline.

In another embodiment, when at least one of the plurality of rotational guides contacts a feature on the interior surface of the pipeline, a first sensor of the plurality of sensors can tilt relative to the longitudinal axis of the pipeline from an initial position to a deviated position while at least one of the other plurality of sensors is in the initial position when sensing the parameter of the pipeline wall.

In another embodiment, the parameter can be at least one of a thickness of a portion of the pipeline, one or more cracks in the pipeline, and a size of the one or more cracks in the pipeline.

In another embodiment, the method can also include substantially maintaining the standoff distance between each sensor and the interior surface of the pipeline wall as the at least one sensor module translates through the pipeline.

In another embodiment, the method can include maintaining a predetermined inclination angle between each sensor and the interior surface of the pipeline wall as the at least one sensor module translates through the pipeline.

BRIEF DESCRIPTION OF THE DRAWINGS

These and other features will be more readily understood from the following detailed description taken in conjunction with the accompanying drawings, in which.

Figure 1:
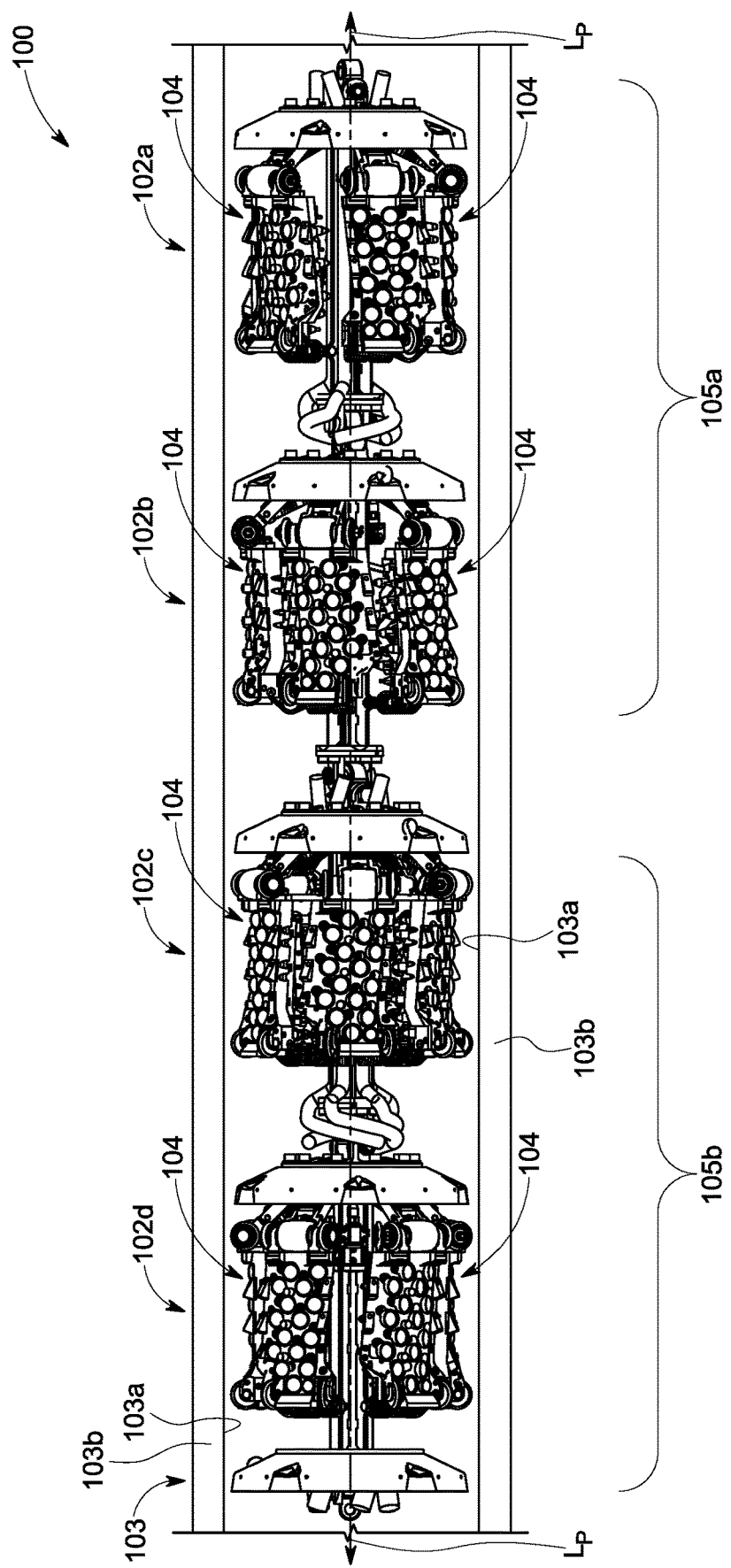
FIG. 1 is a side perspective view of a portion of a pipeline inspection system including four in-line sensor modules within a portion of a pipeline.

It is noted that the drawings are not necessarily to scale. The drawings are intended to depict only typical aspects of the subject matter disclosed herein, and therefore should not be considered as limiting the scope of the disclosure. Those skilled in the art will understand that the systems, devices, and methods specifically described herein and illustrated in the accompanying drawings are non-limiting exemplary embodiments and that the scope of the present invention is defined solely by the claims.

DETAILED DESCRIPTION

Inspection of a pipeline for transporting fluids, such as natural gas, oil, water, etc., can be periodically performed to detect cracks, corrosion, and/or other defects in a wall of the pipeline. An inspection system, known as a PIG, may be passed through a section of pipeline. These systems can include sensor modules, which can include at least one sensor holder that can be equipped with at least one sensor disposed within at least one skid. The skids can come in contact with an interior wall of the pipeline as the sensor module moves through the pipeline, and therefore set a standoff distance between the sensors and the interior wall of the pipeline. However, as the sensor module passes through the pipeline, the skids can deteriorate (e.g., can wear down) and this deterioration can cause the sensor holders to separate from the pipeline wall, change the set inclination angle of the sensors, and/or change the standoff distance. Any of these changes can introduce error into measurements acquired by the sensors, which can cause data to be inaccurate and for defect features to be incorrectly identified and/or measured.

Sensor measurements can be improved if the set standoff distances and set inclination angles of the sensors can be substantially maintained while the sensor module translates through the pipeline. Additionally, reducing the number of sensors that are affected (e.g., tilted) when the sensor module comes into contact with a feature of the pipeline wall (e.g., a protrusion from or a recess in the pipeline wall) can also improve sensor measurements. Accordingly, sensor modules are provided that can include sensor holders each having features that facilitate maintaining set standoff distances and set inclination angles of the sensors with respect to the interior wall of the pipeline during inspection.

In certain embodiments, a sensor module can include a plurality of sensor holders. Each sensor holder can include a holder body with sensors in which the holder body pivots in its long direction (e.g., about a longitudinal axis of the holder body). The sensor holders can also include rotational guides coupled to the holder body and biased toward the interior pipeline wall to define the distance between the sensors and the pipeline wall. The ability of the holder body to pivot can increase stability of its respective sensor holder, by keeping the rotational guides in contact with the pipeline wall. So configured, the predetermined inclination angle of the sensors can be substantially maintained as the sensor module translates through the pipeline. Increased stability provided to the sensor holders can facilitate accurate sensor positioning, and consequently, improve the accuracy of sensor measurements.

FIG. 1 illustrates a portion of a pipeline inspection system. The system 100 can include at least one sensor module, such as a series of four sensor modules 102a, 102b, 102c, 102d that are coupled for movement along a pipeline 103 (e.g., an interior surface 103a of a pipeline wall 103b).

As shown, sensor module 102a is the leading or downstream sensor module, with sensor modules 102b, 102c, 102d subsequently arranged in sequence and sensor module 102d as the trailing or upstream sensor module. As such, the sensor module 102a is downstream of sensor modules 102b, 102c, 102d, and sensor module 102d is upstream of sensor modules 102a, 102b, 102c. As discussed in more detail below, each sensor module shown in FIG. 1 includes a plurality of sensor holders 104 each having a holder body 112 with a plurality of sensors 114, a plurality of rotational guides 118, and a drawbar 119.

As shown in FIG. 1, respective sensors of sensor modules 102a and 102b, collectively referred to herein as a downstream sensor module group 105a, are oriented at a first oblique angle relative to a surface normal aligned with a predetermined axis (e.g., a surface normal to the pipeline wall 103b) of the pipeline wall 103b. Further, respective sensors of sensor modules 102c and 102d, collectively referred to herein as an upstream sensor module group 105b, are oriented at a second oblique angle relative to the surface normal aligned with the predetermined axis (e.g., the surface normal to the pipeline wall 103b) in which the second oblique angle is opposite the first oblique angle. It should be noted that a downstream direction can refer to a direction of translation of system 100 (e.g., through the pipeline 103). Thus, in FIG. 1, the sensor modules 102a, 102b, 102c, 102d, are shown to be translating through the pipeline 103 in a downstream direction. As such, in FIG. 1, the sensor module group 105a is downstream relative to the sensor module group 105b.

Further, as shown, for example, in FIG. 1, for each sensor module the sensor holders 104 are spaced radially around the sensor module and therefore each sensor module has a zone of non-coverage with respect to the internal surface 103a of the pipeline wall 103b along which the sensor modules travels. As such, in FIG. 1, for each sensor module group to provide about 360 degrees of inspection coverage of the pipeline wall 103b, the sensor holders 104 of each module within each sensor module group are positioned out of phase. That is, with respect to the downstream sensor module group 105a, the sensor holders 104 of the first module 102a are out of phase with the sensor holders 104 of the second module 102b. Likewise, with respect to the upstream sensor module group 105b, the sensor holders 104 of the third module 102c are out of phase with the sensor holders 104 of the fourth module 102d. It is also contemplated herein that the pipeline inspection system 100 can also include one or more additional modules, such as a tow (or battery module) and a circuitry module that are connected together and the circuitry module being coupled to a sensor module, such as sensor module 102a.

Figure 2:
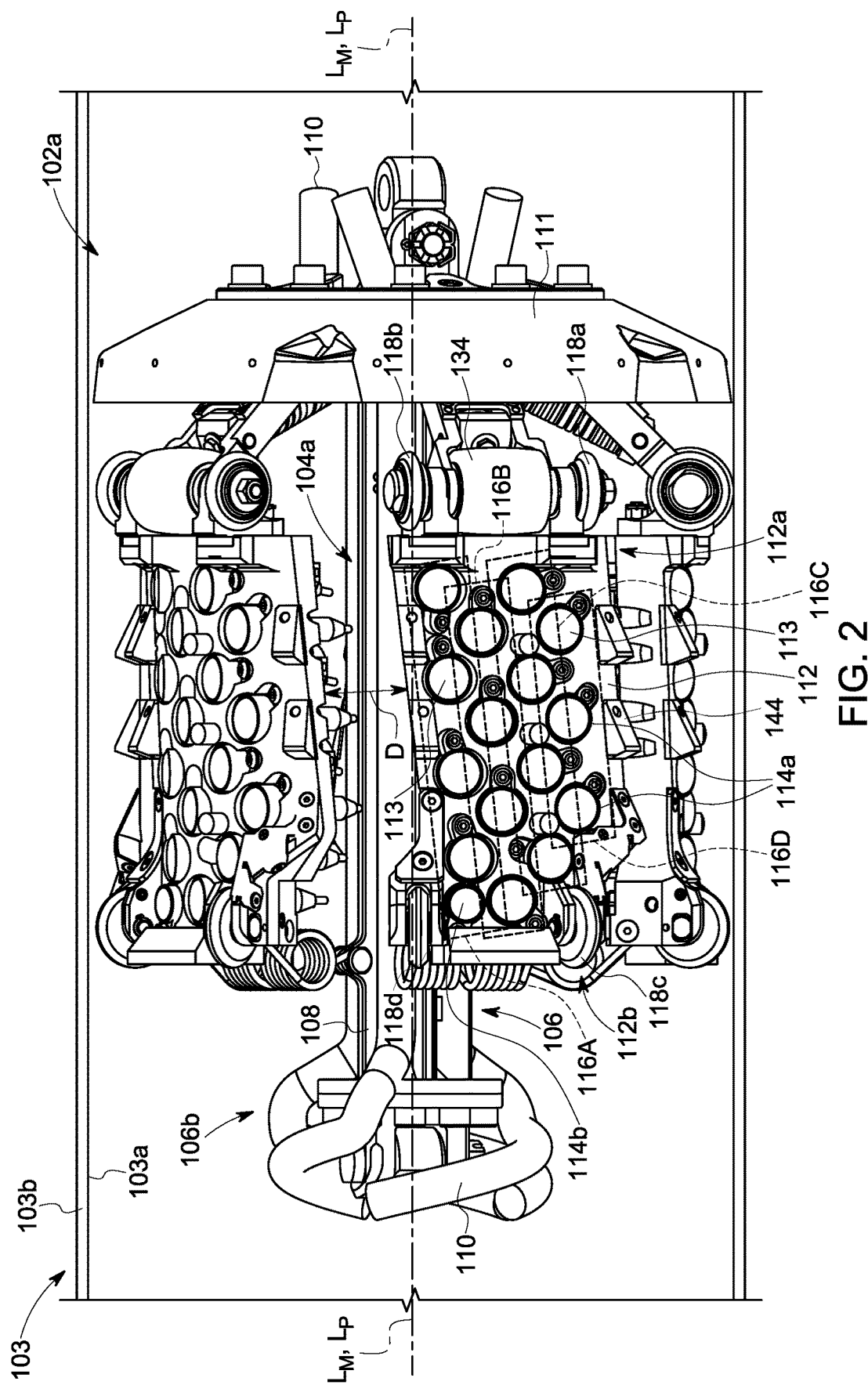
FIG. 2 is a magnified side perspective view of one of the sensor modules having five sensor holders and disposed within the portion of the pipeline shown in FIG. 1.
Figure 3:
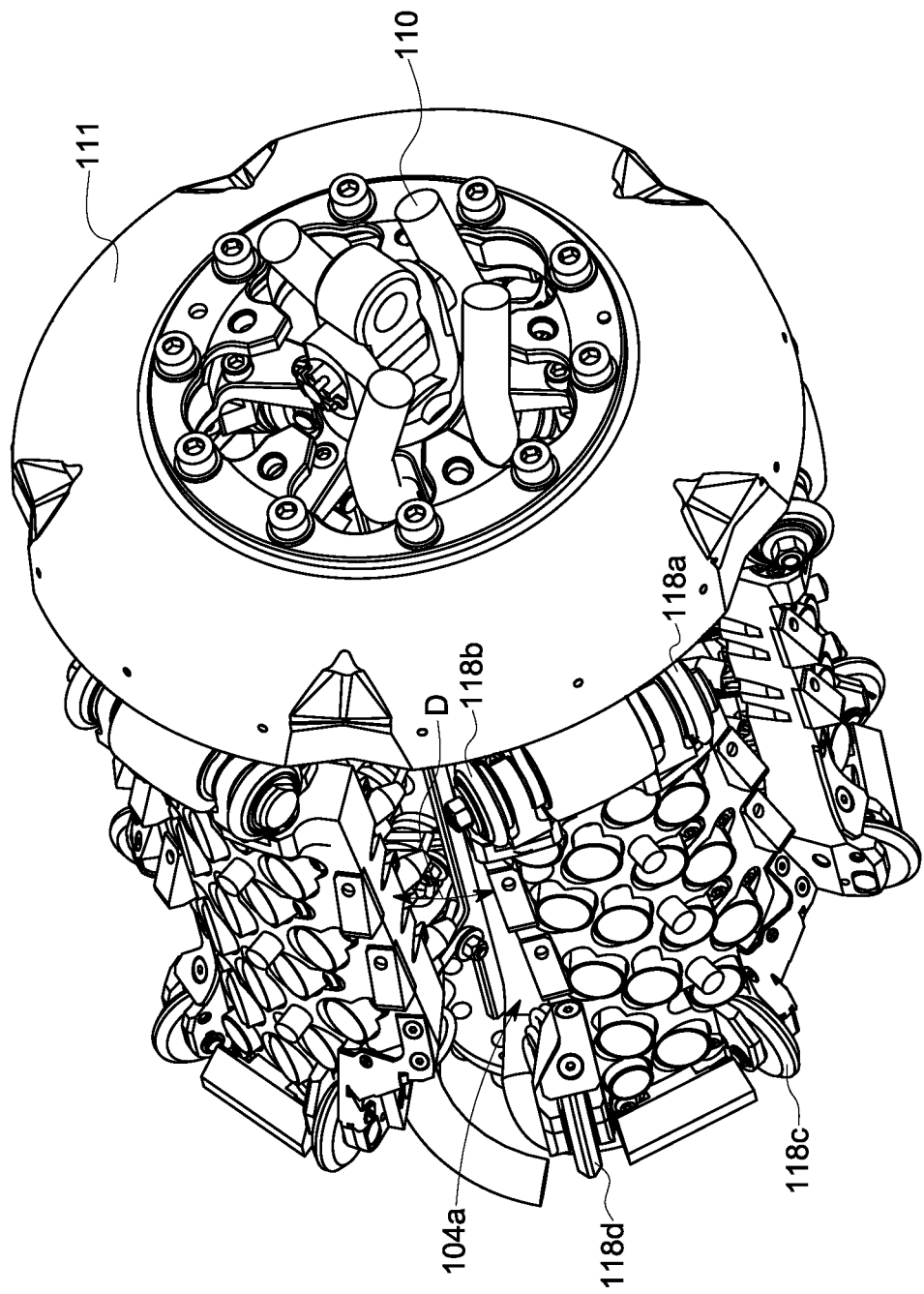
FIG. 3 is a front perspective view of the sensor module shown in FIG. 2 without being disposed in the portion of the pipeline.
Figure 4:
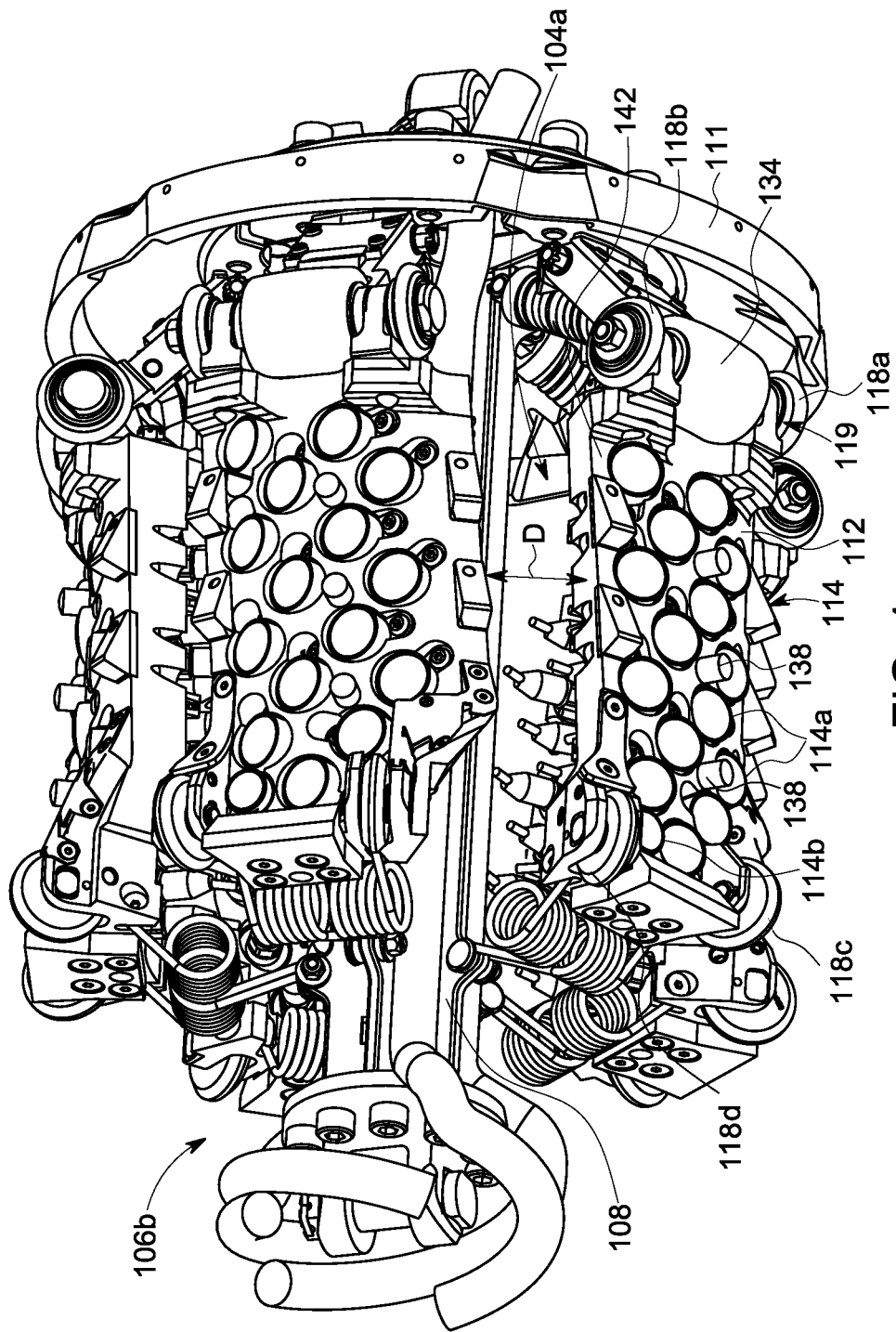
FIG. 4 is a back perspective view of the sensor module shown in FIG. 3.

FIGS. 2-4 show the first sensor module 102a positioned within the pipeline 103 and decoupled from the pipeline inspection system 100. The sensor module 102a has a module body 106 having a first module end 106a and a second module end 106b with a module longitudinal axis ($L_M$) extended therebetween. While the module body 106 can have a variety of configurations, in some embodiments, as shown in FIGS. 2-4, the module body 106 includes an elongated tubular member 108 that extends between the first module end 106a and the second module end 106b with cables 110 disposed therethrough.

As shown, the sensor module 102a includes a sealing/supporting member 111 that can create a seal between the sensor module 102a and the interior surface 103a of the pipeline wall 103b. The sealing/supporting member 111 can also be configured to provide support for, and center, the sensor module 102a within the pipeline 103 as the sensor module 102a translates therethrough. That is, the supporting member 111 can align and overlap the module longitudinal axis ($L_M$) with the pipeline longitudinal axis ($L_P$). This overlapping alignment can help to prevent the sensor module 102a from sagging, which can cause inaccurate sensor measurements of pipeline properties. While the supporting member 111 can have a variety of configurations, as shown in FIGS. 2-4, the supporting member 111 is a disc-shaped, annular structure that is coupled to the sensor module 102a at the first module end 106a.

The sensor module 102a can also include a plurality of sensor holders 104. The sensor module 102a can include any suitable number of sensor holders, and therefore is not limited to the number of sensors holders illustrated herein. It can be appreciated that the number of sensor holders can be based at least in part on a desired size and shape of the sensor module. For example, in some embodiments, the plurality of sensors holders 104 can include about 2 to 50 sensor holders. In other embodiments, the plurality of sensors holders 104 can include about 2 to 15 sensor holders or about 8 to 50 sensor holders.

In some embodiments, as shown in FIGS. 2-4, the plurality of sensor holders 104 includes five sensor holders that are radially arranged about the module longitudinal axis ($L_M$) of the sensor module 102a. The five holders can be spaced a distance apart from each other, such as distance (D) shown in FIGS. 2-4. In some configurations, as shown in FIGS. 2-4, each sensor holder 104 is equally spaced from one another. It is therefore contemplated herein that the distance between sensor holders can vary. Further, it can be appreciated that the distance between adjacent sensor holders can be based at least in part on the desired size and shape of the sensor module. In some embodiments, adjacent sensor holders are spaced apart from one another at a distance from the range of about 150 mm to 1 mm.

Figure 5:
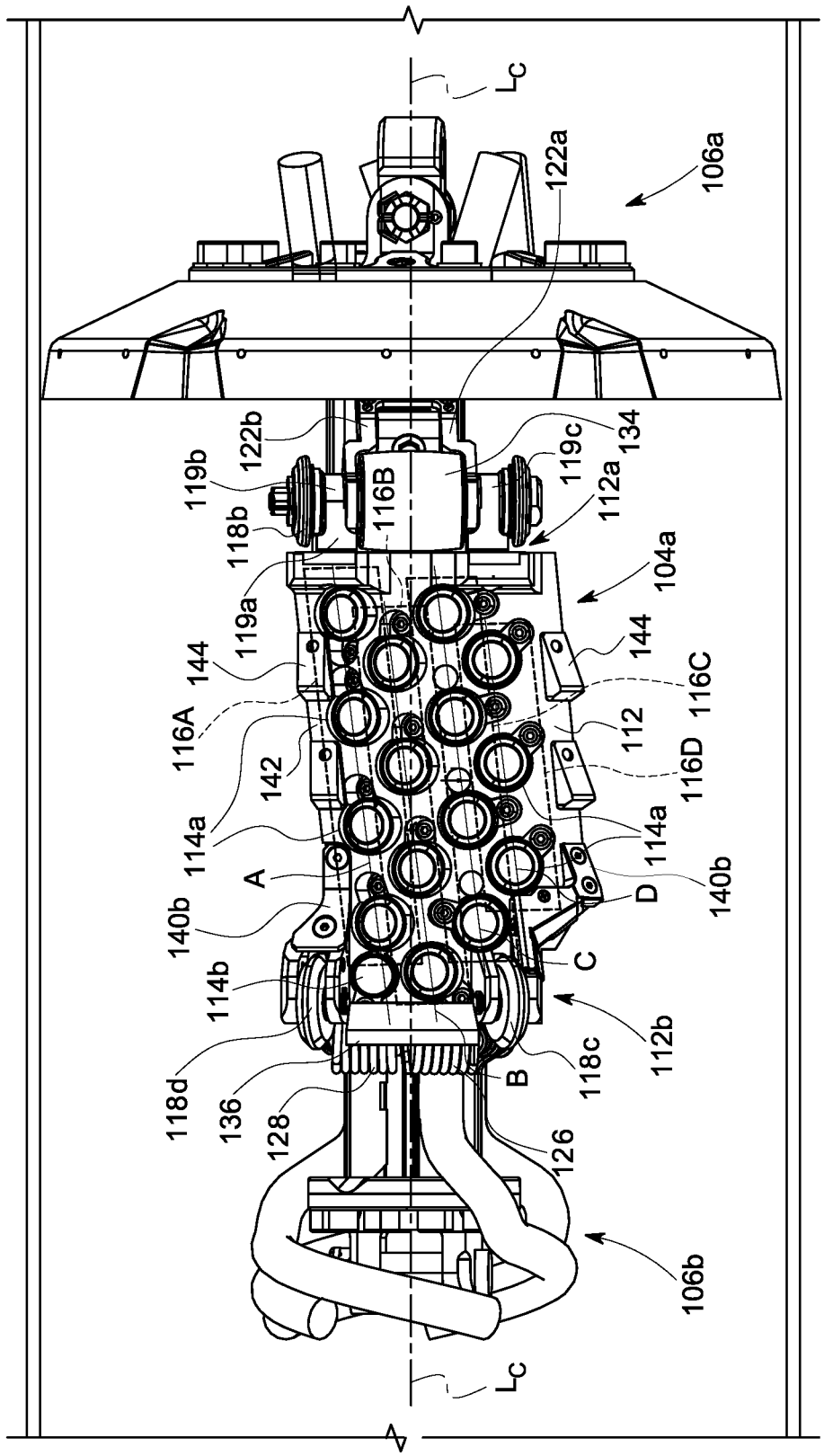
FIG. 5 is a top perspective top view of one of the sensor holders coupled to the sensor module shown in FIGS. 2-4.
Figure 6:
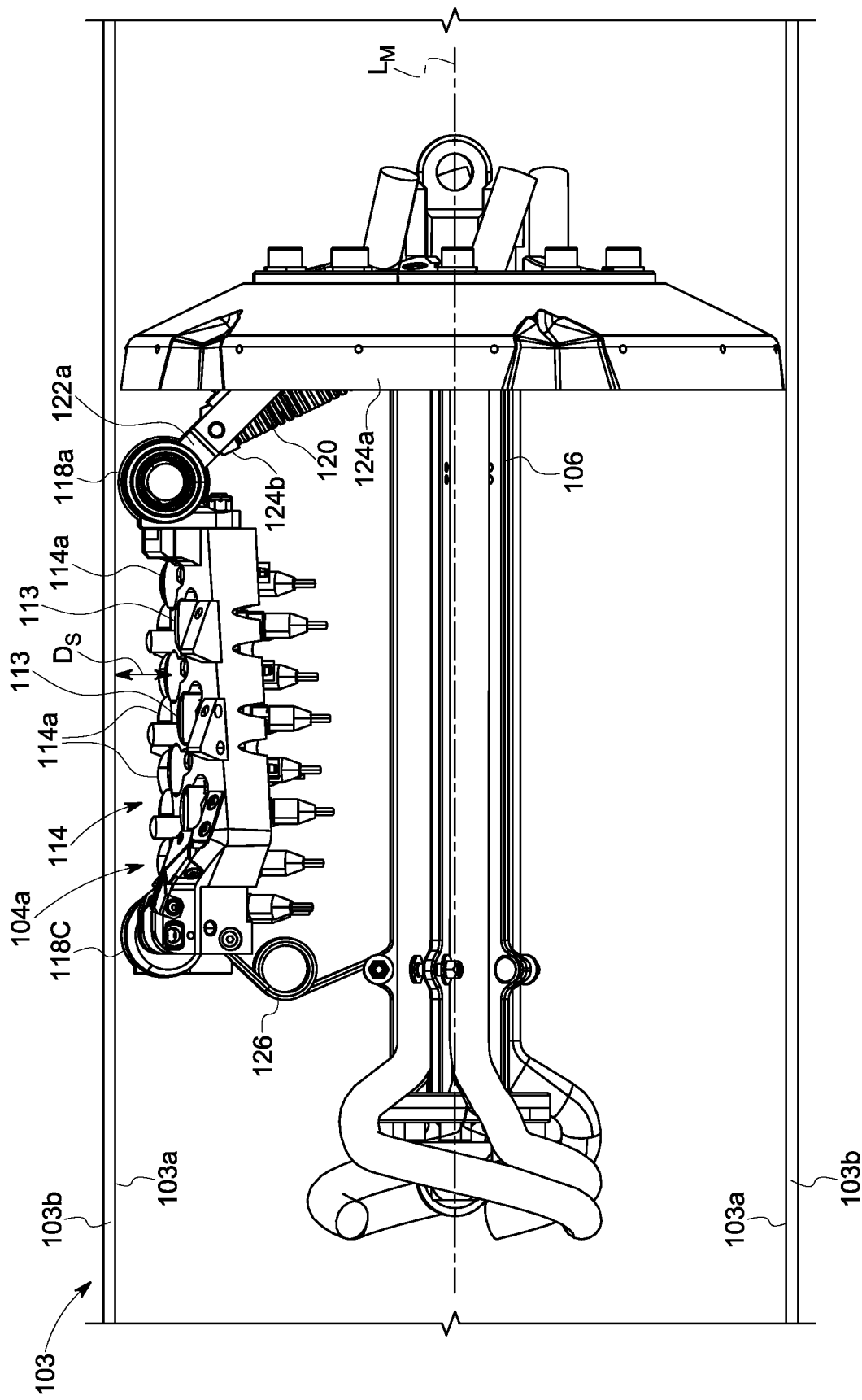
FIG. 6 is a side perspective side view of the one sensor holder coupled to the sensor module shown in FIG. 5.

While five sensor holders are illustrated in FIGS. 2-4, for clarity of the following discussion, reference is made to aspects of a single sensor holder 104a. It can be understood that the following discussion is applicable to the other sensor holders of the sensor module 102a. The sensor holder 104a includes a holder body 112 that has a first body end 112a, a second body end 112b, and a longitudinal axis ($L_B$) extending therebetween. While the holder body 112 can have a variety of shapes, in some embodiments, as shown in FIGS. 2-4, the holder body 112 has a generally arcuate configuration which extends in a circumferential direction with respect to the longitudinal axis ($L_B$) of the holder body 112. The sensor holder 104a is shown in more detail in FIGS. 5-6, with some components of the sensor module 102a removed for simplicity.

The holder body 112 can be formed of any suitable material that is substantially rigid with respect to the pipeline wall 103b. For example, in some embodiments, the holder body 112 can be formed of a material having an elastic modulus from the range of about 60 GPa to 500 GPa or from the range of about 3 GPa to 220 GPa. In one embodiment, the holder body 112 is formed of aluminum. In other embodiments, the holder body 112 can be formed of steel, titanium, magnesium, ceramics, plastic or reinforced plastic. The rigidity of the holder body 112 can help prevent the inclination angles of the sensor facing surfaces 113 of the sensors 114 from changing with respect to the predetermined inclination angle as the sensor module 102*a* translates through the pipeline 103. As a result, the accuracy of the sensor measurements can be improved as compared to the sensor measurements of conventional sensor modules (e.g., sensor modules that include one or more skids). As shown in FIGS. 1-4, the sensor facing surface 113 of each sensor 114 is oriented at an angle relative to the normal vector to the internal surface 103*a* of the pipeline wall 103*b*. As discussed in more detail below, this angle can be a predetermined inclination angle or a companion angle depending on crack orientation.

As shown, the holder body 112 includes a plurality of sensors 114. It will be appreciated that the number of sensors is based at least in part on the size and shape of the holder body. Non-limiting examples of suitable sensors can include various types of ultrasonic sensors, electromagnetic acoustic transducers (EMATs), magnetic flux sensors, etc. In some embodiments, the plurality of sensors 114 can include a group of ultrasonic sensors 114*a*. In such embodiments, the holder body can include from about 5 to 100 ultrasonic sensors. While sensor holders with ultrasonic sensors are shown and described below, it can be appreciated that the sensor holders disclosed herein can be used with other types of sensors without limit.

While the plurality of sensors 114 can have a variety of configurations, in some embodiments, as shown in FIGS. 2-6, each sensor 114 is generally cylindrically shaped. The plurality of sensors 114 can be used to detect the presence of cracks, corrosion, or other features, measure wall-thickness, or otherwise determine the condition of the pipeline. For example, the plurality of sensors 114 can include ultrasonic sensors 114*a* that can emit an ultrasonic signal into the pipeline wall 103*b* and receive reflected ultrasonic signals from the pipeline wall 103*b*. Echoes in the reflected ultrasonic signals may be indicative of a crack, deformity, or other features in the pipeline wall 103*b*. Additionally, the plurality of sensors 114 can include a sensor 114*b* that can be configured to the measure wall thickness of the pipeline wall 103*b*.

The predetermined inclination angle can define the incident angle at which the emitted ultrasonic signal interacts with the interior surface 103*a* of the pipeline wall 103*b*. As such, the accuracy of the sensory measurements can be improved when the predetermined inclination angle can be substantially maintained as the sensor module 102*a* translates through the pipeline 103. The predetermined inclination angle can be any angle that defines a desirable inclination angle such that each ultrasonic sensor 114*a* can accurately detect and measure features of the pipeline wall 103*b* (e.g., one or more cracks, wall thickness, etc). In some embodiments, the predetermined inclination angle can range from about 0.1 degrees to 20 degrees or from about 10 to 35 degrees relative to the normal vector to the internal surface 103*a* of the pipeline wall 103*b*. It can also be understood that in some embodiments, the predetermined inclination angle can be zero.

Figure 7A:
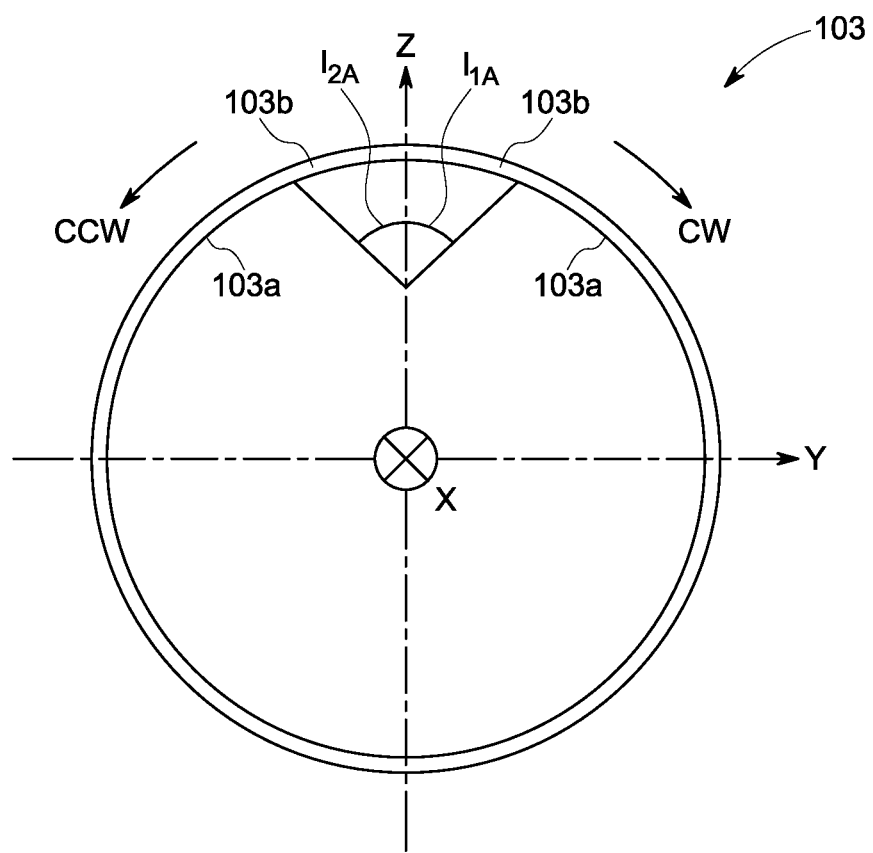
FIG. 7A is a schematic illustrating a cross-sectional view of the pipeline shown in FIG. 1 without the sensor modules, and a first portion of a predetermined inclination angle with respect to a crack extending in a first direction.
Figure 7B:
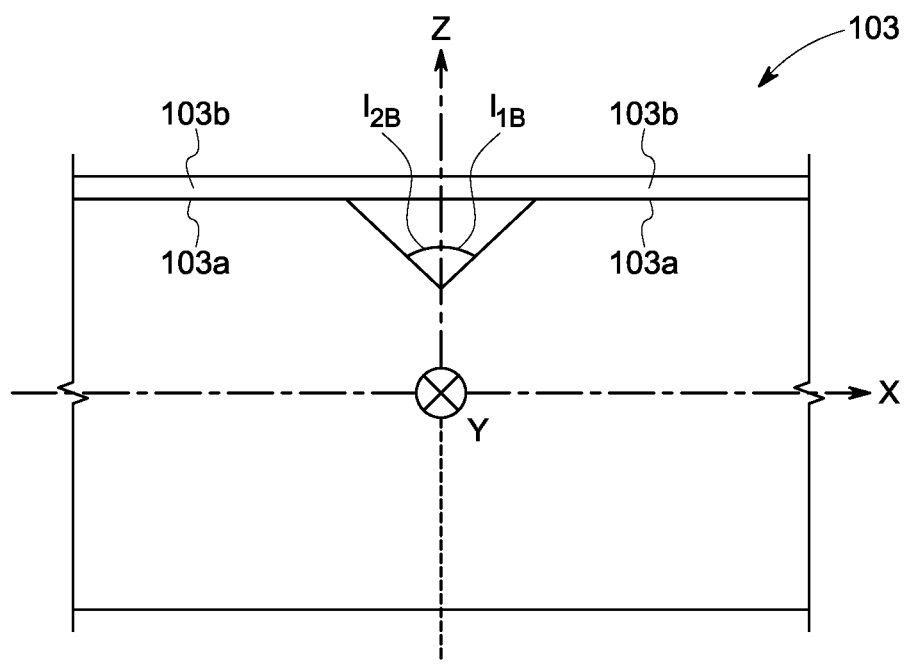
FIG. 7B is a schematic illustrating the pipeline in FIG. 1 without the sensor modules, and a second portion of a predetermined inclination angle with respect to a crack extending in a second direction.

FIGS. 7A-7B illustrate two cross-sectional views of the pipeline without having the sensor module 102*a* disposed therein. FIG. 7A illustrates a first portion of a predetermined inclination angle when a crack is oriented in a first direction, and FIG. 7B illustrates a second portion of a predetermined inclination angle when a crack is oriented in a second direction that is different than the first direction. As such, the predetermined inclination angle is based at least in part on the crack orientation. In one embodiment, a first portion of a predetermined inclination angle ($I_{1A}$ if the sensors are tilted clockwise and $I_{2A}$ if the sensors are tilted counterclockwise in the y-z plane) can be defined as shown in FIG. 7A. In another embodiment, a second portion of a predetermined inclination angle ($I_{1B}$ if the sensors are tilted downstream and $I_{2B}$ if the sensors are tilted upstream in the x-z plane) can be defined as shown in FIG. 7B. It can be appreciated that that a first portion of a predetermined inclination angle and a second portion of a predetermined inclination angle can each have additional components in the respective other planes. That is, a first portion of the predetermined inclination angle in the y-z plane can have an additional component in the x-z plane, and a second portion of the predetermined inclination angle in the x-z plane can have an additional component in the y-z plane. These components in the respective other planes can also have a value of 0. Thus, the predetermined inclination angle is defined with respect to a normal vector coincident to the z-axis, as shown in FIGS. 7A-7B.

The plurality of sensors 114 can be positioned in a predetermined pattern. For example, as shown in FIGS. 2-6, the plurality of ultrasonic sensors 114*a* are divided into four arrays 116A, 116B, 116C, 116D in which each array extends along a corresponding predefined longitudinal axis, such as predefined longitudinal axis A, B, C, and D, respectively. The predetermined pattern is shown in more detail in FIGS. 5-6. Within each array, the sensors 114 are axially offset from each other with respect to their corresponding predefined longitudinal axis. The predetermined pattern can help minimize the number of ultrasonic sensors 114*a* that tilt, and thus deviate from the predetermined inclination angle, for example, in instances where rotational guides 118 at the first body end 112*a* contact either a protrusion extending from the surface of the pipeline or a recess extending beneath the surface of the pipeline wall 103*b*, e.g., a girth weld, as shown in FIGS. 8-11. Further, the predetermined pattern shown in FIGS. 2-6 can employ a greater number of sensors as compared to conventional sensor modules. As such, the sensor module 102*a* can have higher circumferential measurement resolution and thus improved pipeline defect detection capability.

A plurality of rotational guides 118 can be attached to the sensor holder 104*a* and can be designed to contact the interior surface 103*a* of the pipeline wall 103*b*. The rotational guides 118 can be formed of any suitable material that is substantially resistant to abrasion as the rotational guides 118 travel along the interior surface 103*a* of the pipeline wall 103*b*. For example, in some embodiments, the rotational guides 118 are formed of hardened steel. Other non-limiting examples of suitable material for the rotational guides 118 include ceramic, titanium, aluminum, brass, plastic, and reinforced plastic. In some embodiments, the rotational guides 118 can be narrow in width to minimize contact with the interior surface 103*a* of the pipeline wall 103*b*. For example, the rotational guides 118 can have a width of about 2 mm to 15 mm. Further, employing narrow rotational guides 118 can reduce the orientation positions in which the rotational guides 118 travel along a longitudinal seam of the pipeline 103, as discussed in more detail below.

While the plurality of rotational guides 118 may be any rotational structure such as rollers, balls, or wheels, the following discussion will refer to the rotational guides 118 as wheels for simplicity. It can be appreciated that the rotational guides 118 can be replaced with posts or other components that are configured to slide against the interior surface of the pipeline wall.

As shown in FIGS. 2-6, four wheels are coupled to the holder body 112, where two wheels are positioned in front of the plurality of sensors 114 (e.g., at the first body end 112a), and two wheels are positioned in back of the plurality of sensors 114 (e.g., at the second body end 112b). As such, the four wheels are outside of the sensor area, and therefore define the standoff distance ($D_S$) between the plurality of sensors 114 and the interior surface 103a of the pipeline wall 103b. Additionally, the rigidity of the four wheels can also enhance the wheels ability to function as standoff elements. It can be appreciated that "front" and "back" are used herein with reference to the longitudinal travel direction of the sensor holder with respect to the pipeline.

As shown, the first and second wheels 118a, 118b, collectively referred to herein as the front wheels, are coupled to the first body end 112a of the holder body 112, and third and fourth wheels 118c, 118d, collectively referred to herein as the back wheels, are coupled to the second body end 112b of the holder body 112. As discussed above, this wheel positioning allows the four wheels to define the standoff distance of the plurality of sensors 114 relative to the pipeline wall 103b. This wheel positioning relative to the plurality of sensors 114, as shown in FIGS. 2-6 can also help reduce the number of sensors 114 that tilt, and therefore deviate from the predetermined inclination angle, for example, in instances when the front wheels 118a, 118b contact a girth weld (FIGS. 8-11), as discussed in more detail below. Further, when considering a rotation of the sensor module 102a, and thus the sensor holder 104a, in the pipeline while the sensor module 102a translates therethrough, this wheel positioning can allow detection of cracks at a longitudinal seam weld before the sensors 114 are tilted out of position from a wheel finally running on the longitudinal seam weld.

As further shown in FIGS. 2-6, the front wheels 118a, 118b and the back wheels 118c, 118d are longitudinally aligned relative to each other so that the back wheels 118c, 118d follow substantially the same path as the front wheels 118a, 118b when the sensor module 102a translates though the pipeline 103. This wheel alignment can also improve sensor detection of cracks at the longitudinal seam weld by minimizing the amount of times a wheel comes into contact with and runs on the longitudinal seam weld. As such, this wheel alignment and, as discussed above, using narrower wheels can minimize the tilting of sensors. It should be noted that when the system 100 is traveling through the pipeline 103 and a wheel of sensor module 102a is running on a longitudinal seam weld, the area next to the longitudinal seam weld in the pipeline wall 103 can be inspected by sensors of a sensor holder of the sensor module 102c or 102d.

The four wheels can be biased into contact with the interior surface 103a of the pipeline wall. For example, the four wheels can be biased in a radial or outward direction relative to the module longitudinal axis ($L_M$). As shown in FIGS. 2-6, suspension mechanisms are used to bias the four wheels. It can be appreciated that the mechanism(s) used to bias the four wheels are not limited to the illustrated mechanisms, and therefore other suspension mechanisms can be employed with the sensor holder 104a without limit.

As shown in FIGS. 2-6, the first and second wheels 118a, 118b are coupled to a first suspension mechanism that includes a spring-loaded suspension arm 120 that is coupled between the module body 106 of the sensor module 102a and the first body end 112a of the holder body 112. The spring-loaded suspension arm 120 includes two opposing spacer arms 122a, 122b with a spring 124 disposed therebetween. Non-limiting examples of suitable materials forming the spring 124 can include steels. A first end 124a of the spring 124 is coupled to the module body 106 and the second end 124b of the spring 124 is coupled to the two opposing spacer arms 122a, 122b. The two opposing spacer arms 122a, 122b are coupled between the holder body 112 and the module body 106. As such, the spring-loaded suspension arm 120 is configured to pivot relative to the module longitudinal axis ($L_M$). That is, in use, the spring-loaded suspension arm 120 can allow the sensor holder 104a to adjust to changes in the inner diameter of the pipeline. For example, the spring-loaded suspension arm 120 can move the sensor holder 104a radially inward or outward, toward or away from the module longitudinal axis ($L_M$), while still biasing the first and second wheels 118a, 118b in contact with the interior surface 103a of the pipeline wall 103b.

As further shown in FIGS. 2-6, the third and fourth wheels 118c, 118d are coupled to a second suspension mechanism and a third suspension mechanism, respectively. More specifically, as illustrated, the third wheel 118c is coupled to a first interconnected spring 126, such as torsion springs and the like, that is coupled between the module body 106 and the second body end 112b of the holder body 112, and the fourth wheel 118d is coupled to a second interconnected spring 128, such as torsion springs and the like, that is coupled between the module body 106 and the second body end 112b of the holder body 112. As such, the two interconnected springs 126, 128 can allow the sensor holder 104a to adjust to changes in the inner diameter of the pipeline 103 while still biasing the third and fourth wheels 118c, 118d in contact with the interior surface 103a of the pipeline wall 103b.

As discussed above, the pattern of sensors can reduce the number of sensors affected as the sensor module travels along a girth weld. This can be achieved by spacing sensors within an array apart from each other at a distance ("bump length") that is greater than the width of the girth weld. The bump length is longer than the distance of the wheel rolling across the girth weld width. This is because the bump length is also dependent on the travelling speed of the sensor module. Thus, sensors within an array can be positioned at least one bump length apart from each other to increase the number of sensors that can detect the same crack without being displaced due to tilting caused by the wheels of the sensor holder contacting a girth weld.

Figure 8:
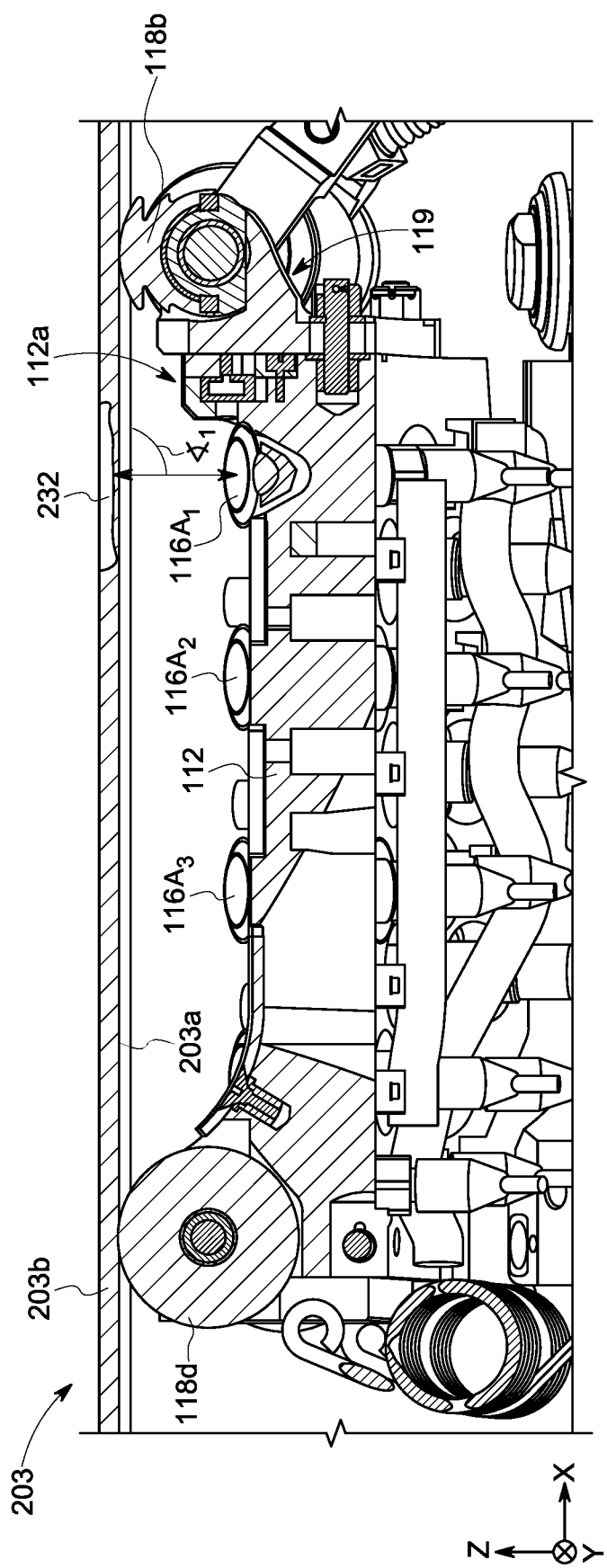
FIG. 8 is a schematic illustrating a cross-sectional view of the sensor module shown in FIGS. 2-4 at a first position within a pipeline.
Figure 9:
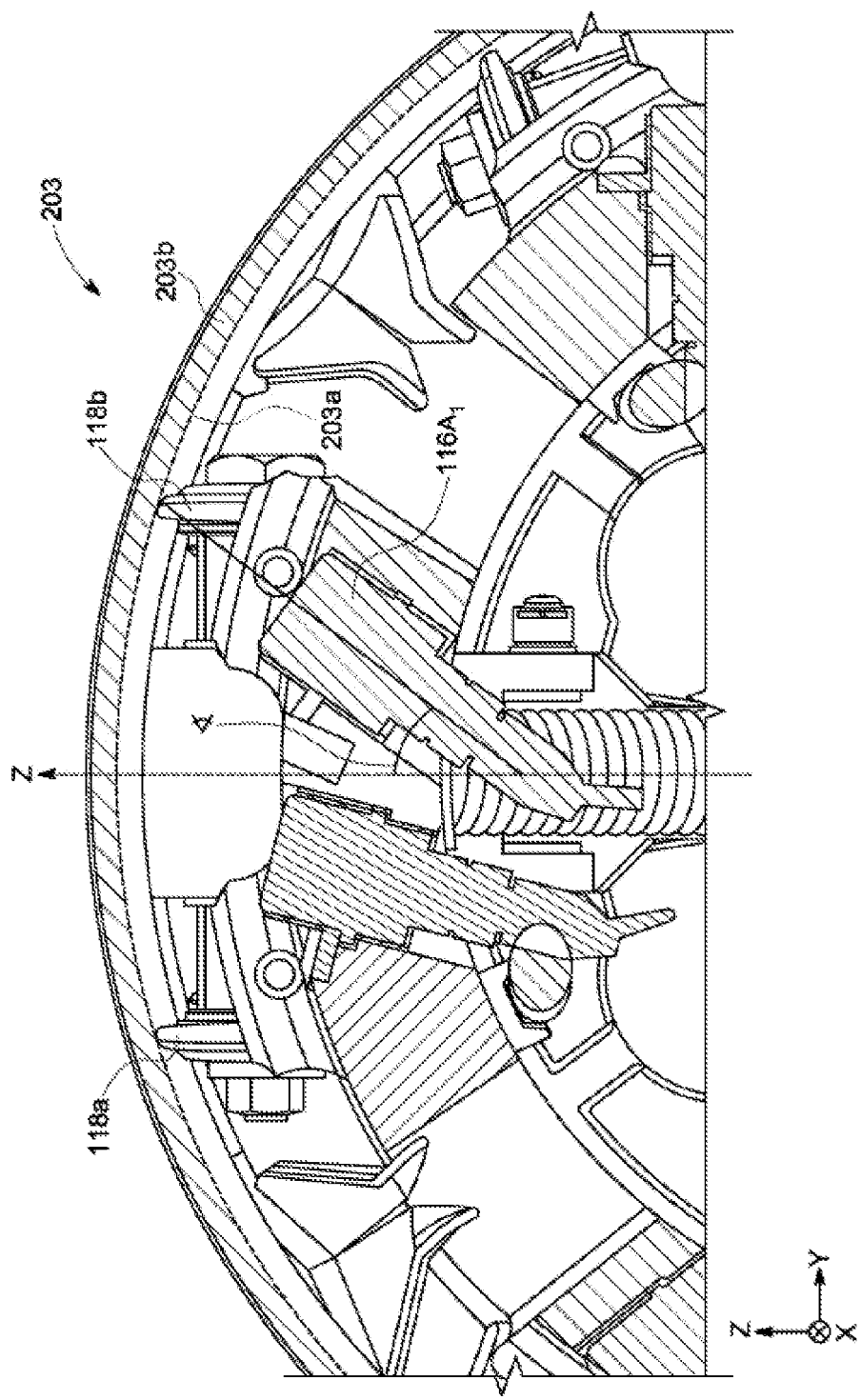
FIG. 9 is another cross-sectional view of the sensor module shown in FIG. 8.
Figure 10:
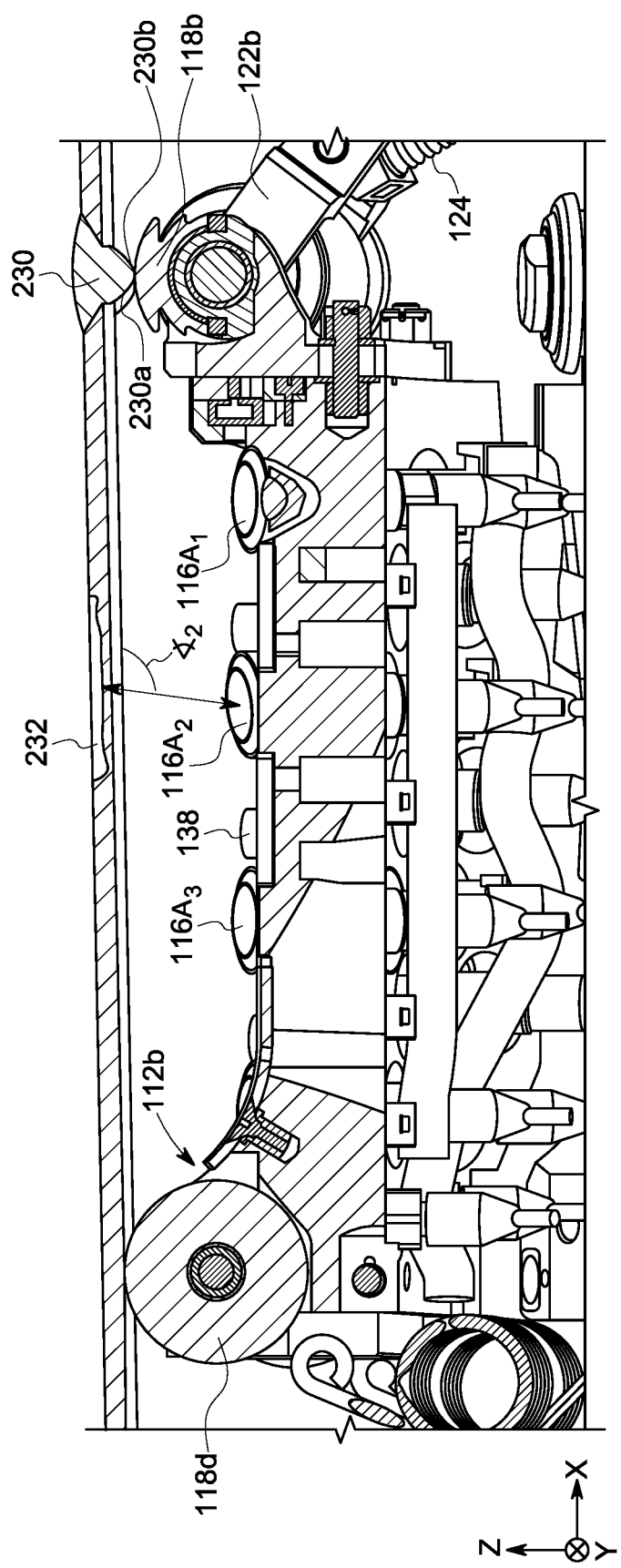
FIG. 10 is a schematic illustrating the sensor module in a downstream position relative to the first position shown in FIG. 8 in which front wheels of the sensor holder contact a girth weld.
Figure 11:
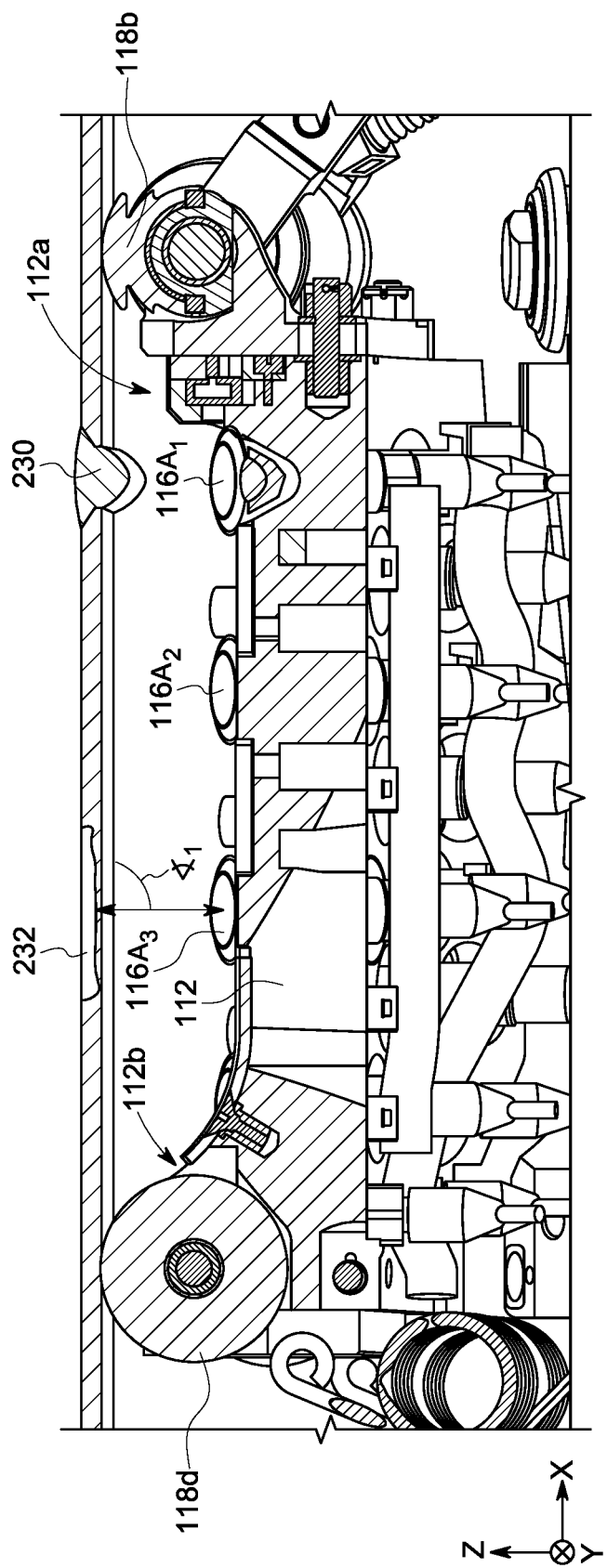
FIG. 11 is a schematic illustrating the sensor module in a further downstream position relative to the downstream position shown in FIG. 10 in which the front wheels of the sensor holder are no longer in contact with the girth weld.

For example, FIGS. 8-11 illustrate sensor module 102a translating through a section of a pipeline 203 in a downstream direction and the effect wheel positioning and the pattern of sensors has on sensor tilting, and thus sensor measurements, as the sensor module 102a passes over a girth weld 230. As shown in FIGS. 8-9, and by way of example, the sensor module 102a translates through the section of the pipeline 203 in which the first sensor $116A_1$ in the first array 116A emits an ultrasonic signal toward the interior surface 203a of the pipeline wall 203b at a suitable first portion of a predetermined inclination angle $\measuredangle$, e.g., an angle with respect to the normal to the interior surface 203a of the pipeline wall 203b in the y-z plane shown in FIG. 9, and a suitable companion angle $\measuredangle$ e.g., an angle with respect to the normal to the interior surface 203a of the pipeline wall 203b in the x-z plane shown in FIG. 8, and therefore accurately detects a crack 232 in the pipeline wall 203b. The sensor module 102a continues to translate through the pipeline 203, as shown in FIG. 10, and the first and second wheels 118a, 118b come into contact with and travel along a first portion 230a of the girth weld 230 until the wheels 118a, 118b reach the highest point 230b of the girth weld 230. This causes the sensors $116A_1$ to $116A_3$ in the first array 116A to tilt out of position and to deviate from the suitable companion angle $\measuredangle_1$. As a result, this tilt causes the sensors $116A_1$ to $116A_3$ in the first array 116A to emit an ultrasonic signal that contacts the interior surface 203a of the pipeline wall 203b at a deviated predetermined inclination angle (not shown in FIG. 10) due to the unsuitable companion angle $\measuredangle_2$, and the second sensor $116A_2$, which at this point in time is in a position to detect the crack 232 in the pipeline wall 203b, thus erroneously detects the crack 232 in the pipeline wall 203b. However, as shown in FIG. 11, at the point in time when the wheels 118a and 118b have crossed the girth weld 230, the sensors $116A_1$ to $116A_3$ in the first array 116A are not affected by the girth weld 230, or the tilting of the sensors $116A_1$ to $116A_3$ induced by the wheels 118a and 118b crossing the girth weld 230 and thus, as the sensor module 102a continues to translate through the pipeline 203, subsequent sensors, such as the third sensor $116A_3$, remain in position. That is, the third sensor $116A_3$ emits an ultrasonic signal toward the interior surface 203a of the pipeline wall 203b at a first portion of a predetermined inclination angle $\measuredangle$ and suitable companion angle $\measuredangle_1$, and therefore accurately detects the crack 232 in the pipeline wall 203b.

As discussed above, and as shown in FIGS. 2-6, the sensor module 102a also includes a drawbar 119 that is coupled to the axle extending through the first and second wheels 118a, 118b and coupled to the first body end 112a of the holder body 112. While the drawbar 119 can have any suitable configuration, in some embodiments, as shown in FIGS. 2-6, the drawbar 119 can be generally u-shaped. For example, the drawbar 119 can include a base 119a and two opposing members 119b, 119c extending therefrom and in an outward direction. As shown, the base 119a is directly coupled to the first body end 112a. The two opposing members 119b, 119c can be directly coupled to the axle that extends through the first and second wheels 118a, 118b. The drawbar 119 can be configured to allow the holder body 112 to at least partially pivot about the longitudinal axis of the holder body ($L_B$). The pivoting of the holder body 112 can cause the four wheels 118a, 118b, 118c, 118d to function as three wheels. As such, this can result in a substantially stable position for the sensor holder 104a relative to the pipeline wall 103b as the sensor module 102a translates through the pipeline 103.

By way of example, in instances where the sensor module 102a encounters a change in pipeline geometry (e.g., bends in a pipeline or non-circular portions of a pipeline, such as an oval), the drawbar 119 can allow the holder body 112 to pivot such that all four wheels 118a, 118b, 118c, 118d can remain in contact with the pipeline wall. For example, as the sensor module 102a travels through a non-circular portion of a pipeline, the interior surface of the pipeline wall can be uneven. Thus, to maintain stability of the holder body 112 on this uneven surface, the drawbar 119 can allow the holder body 112 to pivot such that the holder body 112 does not rock from side to side. That is, the pivoting of the holder body 112 prevents the back wheels 118c, 118d from lifting off the uneven surface and shifting the holder body 112 into an unstable state. As such, having all four wheels 118a, 118b, 188c, 118d in contact with the interior surface of the pipeline wall independent of pipeline geometry, undesirable tilting of the sensors can be minimized. Further, the increase in stiffness of the sensor holder, for example, due to the holder body material and the number of sensors employed, can be at least partially offset by the drawbar 119, and thus by the pivoting ability of the holder body 112.

Additionally or alternatively, the use of the drawbar 119 can compensate for misalignment of the module longitudinal axis and the pipeline longitudinal axis due to sagging of the sensor module as a result of gravity while the sensor module 102a translates through the pipeline 103. Misalignment occurs when the module longitudinal axis does not overlap with the pipeline longitudinal axis. That is, when misalignment occurs, the module longitudinal axis may still run parallel to, but not overlap with, the pipeline longitudinal axis. However, the ability for the holder body 112 to pivot about its longitudinal axis $L_B$, due to the use of the drawbar 119, provides an additional biasing force to the back wheels 118c, 118d so that the back wheels 118c, 118d can remain in contact with the interior surface 103a of pipeline wall 103b.

As further shown in FIGS. 2-6, the sensor holder 104a can include at least one protection member that is configured to prevent damage to the plurality of sensors 114 as the sensor module 102a translates through the pipeline 103. For example, the at least one protection member can address at least one of offtake rims, offtake bars, clapper valves, and gate valve voids. As shown, the at least one protection member includes a deflector roll 134. The deflector roll 134 is tubular shaped and positioned between the first and second wheels 118a, 118b. The same axle that extends through the first and second wheels 118a, 118b also extends though the deflector roll 134. Thus, the deflector roll 134 is configured to rotate about the axle if the deflector roll 134 comes into contact with an obstacle in the pipeline 103 that can potentially damage the plurality of sensors 114. Further, as shown in FIGS. 2-6, the at least one protection member also includes a deflector block 136 that is coupled to the second body end 112a of the holder body 112. As shown, the deflector block 136 is generally rectangular in shape that extends between the third and fourth wheels 118c, 118d.

Alternatively or additionally, the at least one protection member can include protector pins 138, guard plates 140a, 140b, and/or protector fins 144. As shown, for example, the protector pins 138 are generally cylindrically shaped and extend outward from the sensor holder body 112. The guard plates 140a, 140b are laterally displaced relative to the longitudinal axis of the holder body ($L_B$) and each run along a portion of a surface 142 of the sensor holder body 112. The protector fins 144 each extend outwardly from the surface 142 of the sensor holder body 112 at an angle relative to the longitudinal axis of the holder body ($L_B$). It can be appreciated that the protection members are not limited to the structural configurations as illustrated.

The sensor modules can be used to inspect a pipeline using any suitable method. For example in some embodiments, at least one sensor module can be advanced in a downstream direction through a pipeline. The sensor module can have a plurality of sensor holders. Each sensor holder can include a holder body with a plurality of sensors, a plurality of rotational guides that can be biased toward the pipeline wall so as to define a standoff distance between each sensor and an interior surface of the pipeline wall. Each holder body can pivot about a longitudinal axis thereof such that at least one of the plurality of rotational guides remains in contact with the interior surface of the pipeline wall as the at least one sensor module translates through the pipeline.

The method can also include sensing, by the plurality of sensors, a parameter of the pipeline wall as the at least one sensor module translates through the pipeline. In some embodiments, the parameter can be at least one of a thickness of a portion of the pipeline, one or more cracks in the pipeline, and a size of the one or more cracks in the pipeline. In some embodiments, the method can also include substantially maintaining the standoff distance between each sensor and the interior surface of the pipeline wall as the at least one sensor module translates through the pipeline. In some embodiments, the method can also include substantially maintaining a predetermined inclination angle between each sensor and the interior surface of the pipeline wall as the at least one sensor module translates through the pipeline.

In some embodiments, when at least one of the plurality of rotational guides contacts a feature on the interior surface of the pipeline, a first sensor of the plurality of sensors tilts relative to the longitudinal axis of the pipeline from an initial position to a deviated position while at least one of the other plurality of sensors is in the initial position when sensing the parameter of the pipeline wall.

Exemplary technical effects of the methods, systems, and devices described herein include, by way of non-limiting example, the ability to increase circumferential measurement resolution, the prevention of sensor tilting during crack detection through wheel positioning and alignment, maintaining a desired standoff distance between the sensors and the pipeline or maintaining set inclination angles of the sensors through employing guides, such as wheels, that are substantially resistant to abrasion from traveling along the pipeline wall, increased position accuracy of the sensors while sensing close to and at girth welds, minimal sensor tilting when traveling along a longitudinal seam weld and prevent tilted sensors from running next to or at longitudinal seams, and increase the long term capability of the sensor modules to adapt to different inner diameters of pipeline though steel spring loaded suspension.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

Certain exemplary embodiments are described to provide an overview of the principles of the structure, function, manufacture, and use of the systems, devices, and methods disclosed herein. One or more examples of these embodiments are illustrated in the accompanying drawings. The features illustrated or described in connection with one exemplary embodiment can be combined with the features of other embodiments. Such modifications and variations are intended to be included within the scope of the present invention. Further, in the present disclosure, like-named components of the embodiments generally have similar features, and thus within a particular embodiment each feature of each like-named component is not necessarily fully elaborated upon.

One skilled in the art will appreciate further features and advantages of the invention based on the above-described embodiments. Accordingly, the present application is not to be limited by what has been particularly shown and described, except as indicated by the appended claims. All publications and references cited herein are expressly incorporated by reference in their entirety.

What is claimed is:

1. A pipeline inspection system, comprising:
   at least one sensor module having a module body extending from a first module end to a second module end, and
   a plurality of sensor holders mounted to the module body, each sensor holder comprising,
      a holder body with a first body end, a second body end, and a plurality of sensors positioned therebetween, the plurality of sensors being configured to sense a parameter of a wall of a pipeline having a longitudinal axis extending therethrough;
      a protection member configured to protect the plurality of sensors from damage as the at least one sensor module translates through the pipeline, the protection member including a tubular-shaped deflector roll and a plurality of protector fins extending outward from a surface of the holder body at an angle relative to a longitudinal axis of the holder body extending between the first body end and the second body end; and
      a plurality of rotational guides coupled to the holder body and configured to be biased towards an interior surface of the pipeline wall so as to define a standoff distance between each sensor and the interior surface of the pipeline wall,
   wherein each sensor holder is at least partially pivotable about the longitudinal axis of the holder body.

2. The system of claim 1, further comprising a drawbar coupled to an axle extending through the first and second rotational guides and coupled to the first body end to allow the holder body to at least partially pivot about the longitudinal axis of the holder body.

3. The system of claim 1, wherein the plurality of rotational guides comprises a first rotational guide and a second rotational guide coupled to the first body end, and a third rotational guide and a fourth rotational guide coupled to the second body end.

4. The system of claim 3, wherein the first and third rotational guides are longitudinally aligned relative to each other such that the third rotational guide follows substantially the same path as the first rotational guide when the at least one sensor module translates through the pipeline.

5. The system of claim 3, wherein the second and fourth rotational guides are longitudinally aligned relative to each other such that the fourth rotational guide follows substantially the same path as the second rotational guide when the at least one sensor module translates through the pipeline.

6. The system of claim 1, wherein the plurality of sensors are positioned in a predetermined pattern such that when at least one of the plurality of rotational guides contacts a feature on the interior surface of a pipeline, a first sensor of the plurality of sensors tilts relative to the longitudinal axis of the pipeline from an initial position to a deviated position while at least one of the other plurality of sensors is in the initial position when sensing the parameter of the pipeline wall.

7. The system of claim 1, wherein each sensor holder includes at least one suspension arm mounted between the module body and the sensor holder, wherein the at least one suspension arm is configured to bias at least one of the plurality of rotational guides into contact with the pipeline wall.

8. The system of claim 1, wherein the at least one sensor module has a module longitudinal axis extending between the first and second module ends, and wherein the at least one sensor module includes a supporting member that is configured to substantially align and overlap the module longitudinal axis with the longitudinal axis of the pipeline when the at least one sensor module is translated through the pipeline.

9. The system of claim 1, wherein the at least one sensor module has a module longitudinal axis extending between the first and second module ends, and wherein the plurality of sensor holders are spaced circumferentially from one another about the longitudinal axis of the at least one sensor module.

10. The system of claim 1, wherein the at least one sensor module includes first and second sensor modules that are axially offset from one another with respect to the longitudinal axis of the pipeline wall.

11. The system of claim 1, wherein the at least one sensor module includes first and second sensor modules, and wherein the plurality of sensor holders of the first sensor module is out of phase with the plurality of sensor holders of the second sensor module such that the system has about 360 degrees of inspection coverage of the pipeline wall when the first and second sensor modules translate through the pipeline.

12. The system of claim 1, wherein the at least one sensor module includes first and second sensor modules, wherein the plurality of sensors of the first sensor module is angled in a first direction and the plurality of sensors of the second sensor module are angled in a second direction opposite the first direction.

13. The system of claim 1, further comprising a sealing member coupled to the at least one sensor module and configured to create a seal between the at least one sensor module and the interior surface of the pipeline wall.

14. A method of inspecting a pipeline, the method comprising:
advancing at least one sensor module in a downstream direction through a pipeline having a longitudinal axis extending therethrough, the at least one sensor module having a plurality of sensor holders, each sensor holder including a holder body with a plurality of sensors positioned between a first holder body end and a second holder body end, each holder body including a plurality of rotational guides that are biased toward a wall of the pipeline so as to define a standoff distance between each sensor and an interior surface of the pipeline wall, wherein each sensor holder includes a protection member configured to protect the plurality of sensors from damage as the at least one sensor module translates through the pipeline, the protection member including, a tubular-shaped deflector roll and a plurality of protector tins extending outward from a surface of the holder body at an angle relative to a longitudinal axis of the holder body extending between the first holder body end and the second holder body end, and each holder body pivoting about the longitudinal axis thereof such that at least one of the plurality of rotational guides remains in contact with the interior surface of the pipeline wall as the at least one sensor module translates through the pipeline; and
sensing, by the plurality of sensors, a parameter of the pipeline wall as the at least one sensor module translates through the pipeline.

15. The method of claim 14, wherein, when at least one of the plurality of rotational guides contacts a feature on the interior surface of the pipeline wall, a first sensor of the plurality of sensors tilts relative to the longitudinal axis of the pipeline from an initial position to a deviated position while at least one of the other plurality of sensors is in the initial position when sensing the parameter of the pipeline wall.

16. The method of claim 15, wherein the parameter is at least one of a thickness of a portion of the pipeline, one or more cracks in the pipeline, or a size of the one or more cracks in the pipeline.

17. The method of claim 14, further comprising substantially maintaining the standoff distance between each sensor and the interior surface of the pipeline wall as the at least one sensor module translates through the pipeline.

18. The method of claim 14, further comprising substantially maintaining a predetermined inclination angle between each sensor and the interior surface of the pipeline wall as the at least one sensor module translates through the pipeline.

* * * * *